United States Patent [19]
Cooke et al.

[11] Patent Number: 6,040,493
[45] Date of Patent: Mar. 21, 2000

[54] BIOREACTOR WOUND DRESSING

[75] Inventors: Randolph L. Cooke, East Amwell Township, Hunterdon County; Vladimir A. Stoy, Princeton Township, Mercer County, both of N.J.

[73] Assignee: Replication Medical, Inc., Rocky Hill, N.J.

[21] Appl. No.: 09/066,146

[22] Filed: Apr. 24, 1998

[51] Int. Cl.[7] .................................................. A61F 13/00
[52] U.S. Cl. .............................. 602/41; 602/42; 602/48; 428/297.1; 428/320.2
[58] Field of Search .................. 602/42, 48, 41; 428/297.1, 320.2

[56] References Cited

U.S. PATENT DOCUMENTS

| Re. 35,399 | 12/1996 | Eisenberg | 623/11 |
|---|---|---|---|
| 4,331,783 | 5/1982 | Stoy | 525/294 |
| 4,337,327 | 6/1982 | Stoy | 525/280 |
| 4,370,451 | 1/1983 | Stoy | 525/294 |
| 4,379,874 | 4/1983 | Stoy | 524/27 |
| 4,420,589 | 12/1983 | Stoy | 525/93 |
| 4,663,358 | 5/1987 | Hyon et al. | 521/64 |
| 4,909,244 | 3/1990 | Quarfoot et al. | 128/156 |
| 4,943,618 | 7/1990 | Stoy et al. | 525/340 |
| 4,979,946 | 12/1990 | Gilman | 604/307 |
| 5,059,424 | 10/1991 | Cartmell et al. | 424/443 |
| 5,076,265 | 12/1991 | Wokalek | 128/156 |
| 5,106,629 | 4/1992 | Cartmell et al. | 424/445 |
| 5,112,618 | 5/1992 | Cartmell et al. | 424/443 |
| 5,115,801 | 5/1992 | Cartmell et al. | 602/48 |
| 5,120,816 | 6/1992 | Gould et al. | 528/76 |
| 5,154,706 | 10/1992 | Cartmell et al. | 604/307 |
| 5,204,110 | 4/1993 | Cartmell et al. | 424/443 |
| 5,252,692 | 10/1993 | Lovy et al. | 526/342 |
| 5,423,736 | 6/1995 | Cartmell et al. | 602/42 |
| 5,423,737 | 6/1995 | Cartmell et al. | 602/57 |
| 5,429,589 | 7/1995 | Cartmell et al. | 602/42 |
| 5,460,939 | 10/1995 | Hansbrough et al. | 435/1.1 |
| 5,476,443 | 12/1995 | Cartmell et al. | 602/58 |
| 5,489,262 | 2/1996 | Cartmell et al. | 602/57 |
| 5,501,661 | 3/1996 | Cartmell et al. | 602/58 |
| 5,531,999 | 7/1996 | Cartmell et al. | 424/445 |
| 5,674,523 | 10/1997 | Cartmell et al. | 424/445 |
| 5,688,855 | 11/1997 | Stoy et al. | 524/505 |
| 5,693,332 | 12/1997 | Hansbrough | 424/426 |
| 5,695,777 | 12/1997 | Donovan et al. | 424/443 |

OTHER PUBLICATIONS

Green, Howard; Cultured Cells for the Treatment of Disease Nov. 1991; p. 96–102; Scientific American.

Duinslaeger et al; Cultured Allogeneic Keratinocyte Sheets Accelerate Healing Compared to Op–Site Treatment of Donor Sites . . . .

Rennekampff et al; Accelular Human Dermis Promotes Cultured Keratinocyte Engraftment; Nov.–Dec. 1997; 535–544.

Hron et al; Silicone Rubber–hydrogel Composites as Polymeric Biomaterials; Feb. 7, 1997; p. 1069–1073; Biomaterials.

Hron et al; Water–swellable Rubbers Containing Powdery Poly(acrylamide) Hydrogel; Jul. 22, 1996; p. 203–210.

*Primary Examiner*—John G. Weiss
*Assistant Examiner*—Kelvin Hart
*Attorney, Agent, or Firm*—Kenneth P. Glynn, Esq.

[57] ABSTRACT

The present invention is a bioreactor wound dressing which includes a first layer, being a transport layer, in direct contact with a wound. It includes at least one layer of a permeable polymeric media containing, in equilibrium with body fluids, at least 40% by weight of liquid, and is impermeable for infectious agents of any kind and being permeable to water soluble substances having molecular weight up to at least 1000 Daltons. There is a second layer, being a fluid reservoir layer that is adjacent to the transport layer and is capable of containing between 40% and 100% of its volume of an aqueous liquid, wherein the transport layer and reservoir layer are permeably interconnected for aqueous solutions and are in a substantial osmotic equilibrium. The invention also includes a method of wound treatment utilizing the bioreactor wound dressing.

13 Claims, 3 Drawing Sheets

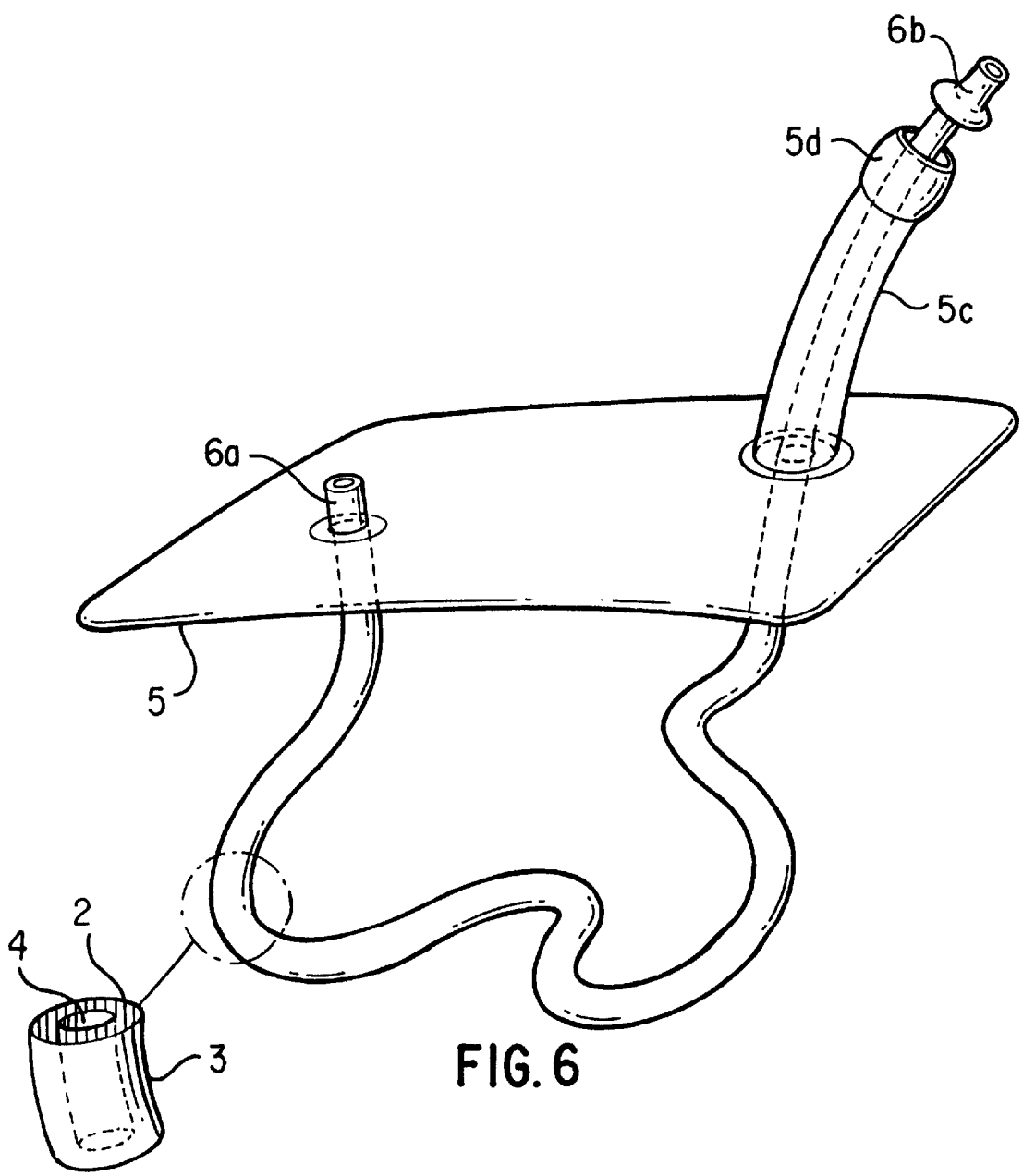

BIOREACTOR WOUND DRESSING

BACKGROUND OF THE INVENTION

1. Field of the Invention

1. The present invention relates to wound dressings and more specifically to bioreactor wound dressings which may be used for intentional wounds—surgical incisions and graftings, as well as accidental and unintentional wounds, including cuts, penetrations, burns, sores, ulcers and other deteriorating or damaged skin and flesh wounds.

2. Information Disclosure Statement

To date, no satisfactory dressing has been developed for difficult wounds, such as deep burns or chronic wounds including decubitus ulcers, venous stasis sores, radiation ulcers, pressure sores, ischemic ulcers or diabetic ulcers. Treatment of these wounds remains a very long and expensive process.

It has been found that moist wounds often heal faster. This can be achieved if the desiccation of the wound is prevented by slowing down evaporation of water from the wound. Numerous types of occlusive wound dressings have been developed that are designed to maintain the favorable moist environment in the wound that is deemed essential for the healing process. These dressings promote formation of granular tissue in the wound bed and facilitate migration of epidermal cells. In addition, the occlusive dressings help to control infections. This leads to faster closure of the wound, less pain and less scarring.

One of the problems of occlusive dressings is accumulation of exudate in certain wound types. The exudate interferes with the dressing adhesion and can be a locus of an infection.

This problem can be partly controlled by using hydrogel occlusive dressings, both in the form of a particulate hydrogel dispersion and hydrogel membranes covering the wound. If dehydrated, hydrogel is able to absorb the excess liquid. Various designs of hydrogel-containing absorptive dressings are described in the U.S. Pat. No. 4,909,244, to Quarfoot et al., describes "A wound dressing adapted for preventing of pooling of wound exudate and for promoting healing which is comprised in the following order: (a) a layer consisting essentially of hydrogel for placement on a wound, the hydrogel being characterized as being wound friendly and for absorbing and acting as a reservoir for wound exudate: (b)an intermediate layer disposed over said hydrogel layer. The intermediate layer comprises a tacky hydrogel or hydrocolloid adhesive, the tack hydrogel or hydrocolloid adhesive characterized as having a greater absorbent capacity that does the hydrogel in the hydrogel layer; the underlying hydrogel layer is characterized as being more friendly and consequently more suitable for direct wound contact than the overlying adhesive hydrogel or greater absorbent capacity; the intermediate layer having sufficient moisture permeability there-through to the surface of the dressing; (c) an outer oxygen- and vapor-permeable layer adapted for transpiration of at least a portion of fluid diffusing through the dressing; U.S. Pat. No. 4,979,946, to the inventor Gilman, describes "The creation of an environmental absorbent dressing having an absorbent layer comprising a hydrogel, and a front sheet comprising a film capable of permitting the passage of liquid covering a front surface of the absorbent layer and coated on the front surface thereof with a porous adhesive; U.S. Pat. No. 5,059,424, to the inventor Cartmell, et al, describes "The creation of a wound dressing product which includes a flexible backing member that can be vacuum formed to include a depression. A pressure sensitive adhesive layer extends across the depression of the flexible backing member and a release liner extends over the exposed pressure sensitive adhesive layer and the exposed hydrogel material, which release liner has a selective releasability whereby it can be removed from the wound dressing product intact, leaving a portion of the pressure sensitive adhesive and the hydrogel material exposed; U.S. Pat. No. 5,076,265, to the inventor Wokalek, describes "The creation of a hydrogel sheet for use as a wound dressing with capillaries permitting wound exudate to pass through the sheet without permitting bacteria to infect the wound. The total cross sectional area of the capillaries represents 0.5 to 3.0 percent of the area of the sheet. The sheets do not stick to the wound surface and allow large quantities of wound exudate to be removed from the wound; U.S. Pat. No. 5,106,629, to the inventor Cartmell et al, describes "The creation of a flexible, transparent wound dressing product containing a clear hydrogel material in a gel-like phase. The wound dressing product is comprised of several layers including a wound dressing, a release layer, and a dimensionally stable backing member. The wound dressing is comprised of a thin film transparent layer having an adhesive perimeter portion and a center portion, and a hydrogel material positioned in the center portion of the transparent layer. Since the wound dressing is transparent, a grid pattern may be printed on the thin film transparent layer to permit measurement of a wound. During manufacture, a vacuum pressure is applied to allow temporary access to the center portion of the thin film transparent layer, creating a cavity for insertion of the hydrogel material. The dimensionally stable backing member is then adhesively attached around the perimeter portion of the thin film transparent layer to help the wound dressing maintain its shape. When the wound dressing product is to be applied to a wound site, the release layer is removed, preferable using an extending tab attached thereto, to expose the hydrogen material. The remaining layers of the wound dressing product are then applied to the wound site, with the hydrogel material directly contacting the wound. Once these layers are in place, the dimensionally stable backing member is removed, preferable using and extending tab attached thereto; U.S. Pat. No. 5,112,618, to the inventor Cartmell et al, describes "The creation of a wound dressing product which includes a flexible backing member that can be vacuum formed to include a depression. A pressure sensitive adhesive layer extends across the depression side of the flexible backing member. A hydrogel material is positioned in the depression of the flexible backing member and a release liner extends over the exposed pressure sensitive adhesive layer and the exposed hydrogel material, which release liner has a selective releasability whereby it can be removed from the wound dressing product intact, leaving a portion of the pressure sensitive adhesive and the hydrogel material exposed; U.S. Pat. No. 5,115,801, to the inventor Cartmell et al, describes The creation of a flexible burn dressing product containing a hydrogel material in a gel-like-phase. The burn dressing product is comprised of several layers including a burn dressing and a release layer. The burn dressing is comprised of a bacterial barrier layer coated with a bonding layer, a reticulated layer impregnated with a hydrogel material, and a hydrogel material layer. A dimensionally stable backing member may also be adhesively attached to the bacterial barrier layer to help the burn dressing maintain its shape until it is applied to a patient. When the burn dressing product is to be applied to a burn site, the release layer is removed to expose the hydrogel material layer. The remaining layers of the burn dressing product are then applied to the burn site, with the hydrogel material layer directly contacting the burn. Once these layers are in place, the dimensionally stable backing member is removed; U.S. Pat. No. 5,154,706, to the inventor Cartmell et al, describes "The creation of a wound dressing for a deep wound comprising of hydrogel layer having an upper and lower surface. The hydrogel layer is correspondingly sized to fill the cavity of the deep wound. The wound dressing further comprises a dressing removal layer disposed between the upper surface and the lower surface of the hydrogel layer. The dressing removal layer. extends outwardly from the hydrogel layer so as to form a pull tab which facilitates removal of the hydrogel layer front the deep wound. A method of making a wound dressing for a deep wound also being provided; U.S. Pat. No. 5,204,110, to the inventor Cartmell et al, describes "The creation of a flexible burn dressing product containing a high absorbency hydrogel material in a gel phase. the hydrogel material is formed from a hydrogel composition for use in a wound dressing. The hydrogel composition is formed from a mixture comprising: (a) from about 0% to about 90% by weight polyhydric alcohol selected from the group consisting of polypropylene glycol, polyethylene glycol and glycerine; (b) from about 6% to about 60% by weight aliphatic diisocyanate terminated prepolymer based on polyols containing more than about 40% polyethelyne oxide and having an isocyanate content of about 3% by weight; (c) from about 4% to about 40% by weight polyethelyne oxide based polyamine; (d) up to about 2% by weight sodium chloride; and (e) the balance water. Such a hydrogel material provides a highly absorbent material capable of retaining large amounts of wound exudate, thereby rendering it very suitable for use in wound dressing; U.S. Pat. No. 5,423,736, to the inventor Cartmell et al, describes "The creation of a wound dressing in the form of a gauze or similar absorbent material having dehydrated hydrogel material impregnated therein for absorbing wound exudate. The dehydrated hydrogel material is formed from an aqueous mixture comprising; (a) from about 0% to 90% by weight polyhydric alcohol; (b) from about 6% to about 60% by weight aliphatic diisocyanate terminated prepolymer; (c) from about 4% to about 40% by weight polyethylene oxide based polyamine; (d) 0% to about 2% by weight sodium chloride and (e) the balance water. The present wound dressing is capable of absorbing large amounts of wound exudate without inhibiting the healing of the wound to which it is contacted since it does not adhere or stick to the wound; U.S. Pat. No. 5,423,737, to the inventor Cartmell et al, describes "The creation of a flexible, transparent wound dressing product containing a clear hydrogel material in a gel-like phase. The wound dressing product is comprised of several layers including a wound dressing, removable tab and release liner. The removable tab provides a grippable surface to allow for the removal of the release liner from the wound dressing and to facilitate handling of the wound dressing during application to the wound site. The tab may be comprised of a flat, double coated paper or other suitable material, or a flexible, V shaped member, and is removable by peeling after the wound dressing is applied. The wound dressing comprises a transparent thin film layer, a first adhesive layer, backing layer, second adhesive layer, support layer and a hydrogel material. The transparent layer has a center portion and a perimeter portion. The backing layer, support layer and hydrogel material, which together from a reinforced hydrogel patch, are positioned in the center portion of the transparent layer. Since the wound dressing is transparent, a grid pattern may be printed on the backing layer to permit measurement of a wound. During manufacture, the hydrogel patch is assembled in sheet form and subsequently cut to a desired size and shape; U.S. Pat. No. 5,429,589, to the inventor Cartmell et al, describes "The creation of a wound dressing in the form of a gauze or similar absorbent material having dehydrated hydrogel material impregnated therein for absorbing wound exudate. The dehydrated hydrogel material is formed from an aqueous mixture comprising; (a) from about 0% to 90% by weight polyhydric alcohol; (b) from about 6% to about 60% by weight aliphatic diisocyanate terminated prepolymer; (c) from about 4% to about 40% by weight polyethylene oxide based polyamine; (d) 0% to about 2% by weight sodium chloride and (e) the balance water. The present wound dressing is capable of absorbing large amounts of wound exudate without inhibiting the healing of the wound to which it is contacted since it does not adhere or stick to such a wound; U.S. Pat. No. 5,476,443, as to the inventor Cartmell et al, describes "The creation of a flexible wound dressing product containing a clear hydrogel material in a gel-like phase. The wound dressing product is comprised of several layers including a wound dressing, optional removable tab and optional release liner. The wound dressing comprises a thin film layer, an adhesive layer, porous backing layer, optional support layer and a hydrogel material. The thin film layer has a center portion and a perimeter portion. the backing layer, support layer and hydrogel material, which together from a reinforced hydrogel patch, are positioned in the center portion of the thin film layer. The porous backing layer is formed of a porous material having sufficient porosity that the backing layer can be secured to the hydrogel material without the use of an adhesive. During the manufacture, the hydrogel patch is assembled in sheet form and subsequently cut to a desired size and shape; U.S. Pat. No. 5,489,262, to the inventor Cartmell et al, describes "The creation of a flexible transparent wound dressing product containing a clear hydrogel material in a gel-like phase; U.S. Pat. No. 5,501,661, to the inventor Cartmell et al, describes a flexible wound dressing product containing a clear hydrogel material in a gel-like phase; U.S. Pat. No. 5,531,999, to the inventor Cartmell et al, describes a hydrogel wound dressing substantially in the form of a rope and also in the form or a strand; U.S. Pat. No. 5,674,523, to the inventor Cartmell et al, describes an elongated, self adhesive wound dressing which includes a hydrogel layer secured to a vapor permeable bacterial barrier layer. The vapor permeable barrier layer possess sufficient porosity such that it readily adheres to the hydrogel layer without the need for an adhesive layer. The wound dressing is adapted to be wrapped around a portion of a patient's body and secured without the use of an adhesive and U.S. Pat. No. 5,695,777, to the inventor Donovan et a, describes "The creation of a wound dressing for use with exuding wounds which including (a) an outer vapor permeable layer permitting transpiration of fluid from the dressing; (b) an intermediate layer of hydrogel adapted for absorbing wound exudate; (c) a wound contacting layer for separating the intermediate hydrogel layer from the wound; (d) wicking means associated with the wound contacting layer for conducting exudate from the wound to the hydrogel; and (e) a therapeutic agent retained in the dressing by the wound contacting layer.

Hydrogels are highly permeable for water and allow it to evaporate from the wound faster than many other materials. However, hydrogel occlusive dressings do have several problems. If they are applied to the wound dehydrated, they remove water from the exudate concentrating proteins and other large biomolecules and thus causing protein denaturation and osmotic imbalance. Hydrogels do not perform too well in the absence of an exudate where the hydrogel is supposed to maintain the moist environment of the wound bed. A dehydrated, or partially hydrated hydrogel cannot be a source of moisture. On the contrary, it tends to compete with the cells for water. Hydrogels are also highly permeable for water so that they form, in itself, a poor moisture barrier. Furthermore, a semihydrated hydrogel typically adheres to the wound bed so that the newly formed tissue is injured during the dressing change. It is rarely recognized that the hydrogel properties can favor the healing only if the hydrogel is fully hydrated. From this follows that various types of occlusive dressings are suitable for some types of the wounds and some phases of the healing (i.e., the exudative phase) but they are unsuitable for others. To complicate the dressing selection, the healing often proceeds through various phases with different exudation rates and different dressing requirements. There is currently no dressing that could satisfactorily control the wound bed conditions, particularly due to the variability of these conditions with time. This requires an occasional change of the dressing as the healing progresses. The dressing change disturbs the healing process and exposes the wound to airborne infections.

For that and other reasons, benefits of occlusive dressings are mostly limited to clean wounds, such as surgical incisions or skin donor sites. Occlusive dressings for chronic and deep burn wounds help to form granular tissue and prevent infections. However, they often do not facilitate the epithelization that is essential for the wound closure.

A standard method of healing deep burns is the application of the split-thickness skin grafts. In this technique, a healthy patient skin is excised, sliced and "expanded" into a mesh to cover a large wound area. This method is laborious and, in some cases, it is difficult to excise a sufficient amount of patient's skin without aggravating his/her condition even further. The graft sometimes does not "take" as it has to cope with infection and necrosis of the underlying tissue. One of the disadvantages is also the cross-hatched pattern left by the autologous graft on the newly formed skin.

These limitations of both current synthetic occlusion dressings and autografts lead to continuing search for better "biological" dressings. It is recognized that healing is a very complicated biological process that benefits from presence of a "scaffolding" or matrix of a connective tissue and various biomolecules (such as growth factors, cytokines, glycoaminoglycans and glycoproteins) supporting and controlling the reconstruction of the skin and of underlying tissues. For that reason, numerous methods were developed involving a processed cadaver skin, porcine skin, or tissue-engineered skin substitutes. The cadaver and porcine skin dressings comprise an acellular dermis, i.e. the full-thickness skin from which epidermis and cells were removed, leaving a collagenous matrix. It is believed that some biological activities remain in this processed skin due to residuals of growth factors, glycoproteins and other biomolecules. The collagen matrix is generally not rejected and can serve as a matrix for the cell growth. However, the process of healing and integration of the matrix into the new tissue is slow and sometimes uncertain.

Another approach is seeding of cells into the wound that are capable of forming the new epidermis. The cells used to close the wound are keratinocytes grown as a tissue culture and forming the cultured epidermal graft. Keratinocytes are harvested from a sample of epidermis (obtained by biopsy) and processed by trypsin that destroys desmosomes interconnecting the keratinocytes without harming the cells. The resulting cell dispersion consists mostly of free keratinocytes, with a minor amount of other cells, such as fibroblasts (cells of connective tissue producing collagen), melanocytes (cells producing pigment melanin) and Langerhans cells (specialized macrophage cells). In human epidermis, keratinocytes are fed by products of fibroblasts from the underlying dermis. Consequently, keratinocytes are generally cultivated on a layer of fibroblasts (typically 3T3 mouse fibroblasts). To prevent the fibroblast proliferation, they are irradiated beforehand by a lethal dose of gamma rays. The dying fibroblasts are seeded on the bottom of cultivation flasks filled with a tissue culture medium containing, inter alia, growth factors and stimulants (cholera toxin, insulin, epidermal growth factor etc.). Keratinocytes are then grown on the top of the 3T3 layer.

Only a small portion of keratinocytes harvested from the skin is capable of proliferation (1–10%). The viable cells form colonies that can be harvested and reseeded. About 70% of the reseeded keratinocytes are capable of multiplication and growth. They gradually grow into a confluent layer of keratinocytes interconnected by desmosomes and adhering to the bottom of the flask. As keratinocytes fill the available area, they start growing into a multi-layered stratified sheet. The surface cells (i.e., those facing the solution and far from the flask bottom) terminally differentiate and flatten to resemble corneocytes. New keratinocytes are formed on the bottom of the sheet.

Once the sheet is formed, it can be detached from the bottom by a neutral protease (dispase). The fragile keratinocyte sheet is lifted and transferred onto a support (such as a gauze with Vaseline). The keratinocyte sheet is then applied as a dressing. Those keratinocytes that "take" are attached to the wound bed, proliferate and differentiate into a new epidermis.

This procedure, described by Howard Green, Scientific American, November 1991, p. 96–102, as currently practiced, has a number of problems. The keratinocyte sheet is very fragile. Keratinocytes have to adhere to a suitable location and have to obtain nutrients quickly to remain viable. The direct contact may be difficult to achieve on the irregular wound surface. The adhesion can be prevented by an exudate, bacterial colonization, necrotic tissue or poorly developed granular tissue. The removal of the dressings can damage the newly formed epidermal layer.

The keratinocytes can be obtained from the patient's own epidermis and form a cultured autograft. This is used mainly in treatment of full-thickness skin wounds. This is not very convenient since the cultivation takes approximately 14 to 21 days and is very expensive.

It was found that similar results can be achieved even using keratinocytes from another person, i.e. forming a cultured allograft. (see, for instance: L. A. Y. Duinslaeger et al, Journal of Burn Care & Rehabilitation, November/December 1997, pp. 545–551.) It was observed that Langerhans cells disappear from the tissue culture after about one week. Consequently, even foreign keratinocytes do not elicit a strong rejection if applied as an allograft. Allogeneous keratinocytes do not survive in the wound for long but their presence supports and accelerates healing, probably due to growth factors and cytokines released by them. Keratinocytes for allograft are often harvested from newborn foreskins to maximize the viability and to minimize the probability of transmission of disease.

It was found that keratinocytes can be advantageously grown on a support (such as a polymeric membrane) that can be directly applied to the wound as a dressing. The membrane is advantageously made from a hydrophilic polymer permeable for water that facilitates the exudate removal from the wound (U.S. Pat. No. 5,693,332, to the inventor Hansbrough, describes keratinocytes supported on a hydrophilic membrane). This way, one can avoid the enzymatic detachment of the keratinocyte sheet from the flask and its handling is greatly facilitated. However, this approach has still several problems. The first problem relates to the fact that keratinocytes grown on the polymeric support are nutrified from the solution, i.e. from the other side than in a living skin where they are fed from the dermis underneath. The polymeric membranes used so far are poorly permeable for nutrients and non-permeable for biomolecules, such as growth factors and cytokines. Therefore, the growth on the polymeric support has to be interrupted before or just after the keratinocytes reach confluence so that their upper layers would not interfere with nutrification of the base layer. This limits the efficacy of the keratinocyte cultivation and delivery.

The second problem derives from the requirement that keratinocytes should adhere well to the support to grow and multiply properly. However, as long as they firmly adhere to the polymeric membrane, they are not released to seed the wound. The active biomolecules from the attached keratinocytes can reach the wound bed by diffusion only and their efficacy is thus diminished.

The third problem is that as keratinocytes are applied to the wound, they are transferred from the nutrient solution optimized for their cultivation to the wound bed that is not necessarily a good environment for the keratinocyte growth. It has been reported that less that 10% of autogenous kerationocytes survive this transfer from cultivation media to the wound.

Highly hydrated, well permeable hydrogels are typically a poor support for tissue cultures. Tissue cells do not adhere to them and if they do, they adhere weakly, do not spread and maintain their rounded shape and are unsuitable for their proliferation. This can be explained by highly hydrated. surfaces of such hydrogels that lack hydrophobic attachment points necessary for both attachment of cells, their spreading and adsorption of the underlying proteins. Because of that, keratinocytes have to be cultivated on more. hydrophobic surfaces of partly hydophilized plastics or "marginal" hydrogels with a low water content and low permeability for nutrients. Hydrogels with a low water content are not permeable for many of the nutrients and factors required by keratinocytes, so that they can provide only a limited support for their growth both during the cultivation and after their transfer to the wound. Moreover, hydrogels with a low water content are typically rather rigid so that they cannot conform well to the uneven surface of the wound.

This illustrates the difficulty in meeting all the contradicting requirements with a single polymeric material in the form of a simple polymeric membrane used as the dressing.

Acellular dermis (such as porcine or cadaver dermis) was recently used as the support for the cultured kerationocytes (Hans O. Rennekampff et al, Journal of Burn Care & Rehabilitation, November/December 1997, pp. 535–544; E. Matouskova et al, British Journal of Dermatology 1997; 136:901–907). Keratinocytes adhere firmly to and grow well on the dermis that provides the scaffold, nutrients and growth factors for the keratinocytes as well as occlusive cover and protection to the wound. However, it has also several disadvantages, such as possibility of the infection transmission, possibility of immune reaction, limited range of mechanical and diffusion properties, high handling costs, non-transparency, etc.

Another approach is development of living skin equivalents by tissue engineering methods, such as U.S. Pat. No. Re. 35,399, to the inventor Eisenberg describes "The creation of a composite living skin equivalent comprising of an epidermal layer of cultured keratinocyte cells, al layer of non-porous collagen and a dermal layer of cultured fibroblast cells in a porous cross-linked collagen sponge matrix. Preferable the non-potous collagen is Type 1, Type 3 or mixtures of Types 1 and 3 bovine collagen, which has been pepsin treated. A process for preparing the skin equivalent is described, as well as a test kit for in vitro testing of the skin equivalent. The skin equivalent has use for skin grafting as well as in vitro testing of the effects of various substances on skin." and U.S. Pat. No. 5,460,939, to the inventor Hansbrough et al, describes "The creation of a living skin replacement. in particular, it relates to a biosynthetic dressing material composed of a living stromal tissue prepared from stromal cells such as fibroblasts cultured upon a three dimensional framework and a transitional covering which acts as an epidermal replacement. Such a living skin replacement provides long term biologic coverage of full thickness wound defects. Since human fibroblasts are known to be relatively non-antigenic when transferred to allogeneic hosts, a temporary living skin replacement made up of such cells attached to a transitional covering may replace the use of cadaveric skin allografts for achieving temporary wound closure in cases where the patients lack enough healthy skin for autografts." The disadvantage of such dressings is very high cost and poor shelf life.

PRESENT INVENTION

The dressing includes a permeable transport layer which is in the direct contact with a wound, and a reservoir layer containing an aqueous liquid with substances beneficial for the healing which are transported through the transport layer into the wound. Substances undesirable for the healing may be removed from the wound into the reservoir layer through the transport layer. The transport is driven either by a concentration gradient (i.e., diffusive permeability) or by a pressure gradient (i.e., hydraulic permeability). Optionally, the dressing also includes an outside protective layer and as well as a mechanism for exchange of the liquid inside the reservoir layer. The dressing is used for protection of wounds, for control of conditions (such as water content, osmolarity, pH) in wounds, for delivery of bioactive substances into wounds, for removal of harmful substances from wounds, for cultivation of human keratinocytes and other cells in vitro and for transport of such cultured cells into wounds, and for protection and support of the human cells proliferating in wounds.

All of these functions, as well as visual inspection of wounds, can be performed without interrupting the protective contact between the present invention transport layer and the wounds.

Thus, the wound dressing according to this Invention includes at least two layers, wherein the first layer is the transport layer designed for the direct contact with the wound and contains at least one layer of a permeable polymeric media containing, in equilibrium with body fluids, at least 40% by weight of liquid and is permeable for water soluble substances having molecular weight higher than 1000 Daltons, constituting, in part, a cultivation sublayer; and the second layer is the reservoir layer that is adjacent to the transport layer and is capable of having between 50% and 100% of its volume occupied by an aqueous liquid.

The transport layer and the reservoir layer are in a substantial osmotic equilibrium. The permeable polymeric medium is preferably a hydrogel.

The dressing according to this Invention is used as an occlusive dressing with a direct control of variable conditions in the wound bed environment. The dressing is also used for controlled delivery of drugs and other bioactive substances directly into the wound. Furthermore, the dressing is used to remove undesirable substances, such as excess of liquids, from the wound. The dressing is also used for cultivation of fibroblasts, keratinocytes and other cells in vitro and for transfer and seeding of cultured cells into the wound.

DESCRIPTION OF DRAWINGS

BRIEF DESCRIPTION OF THE DRAWINGS

Figure 1:
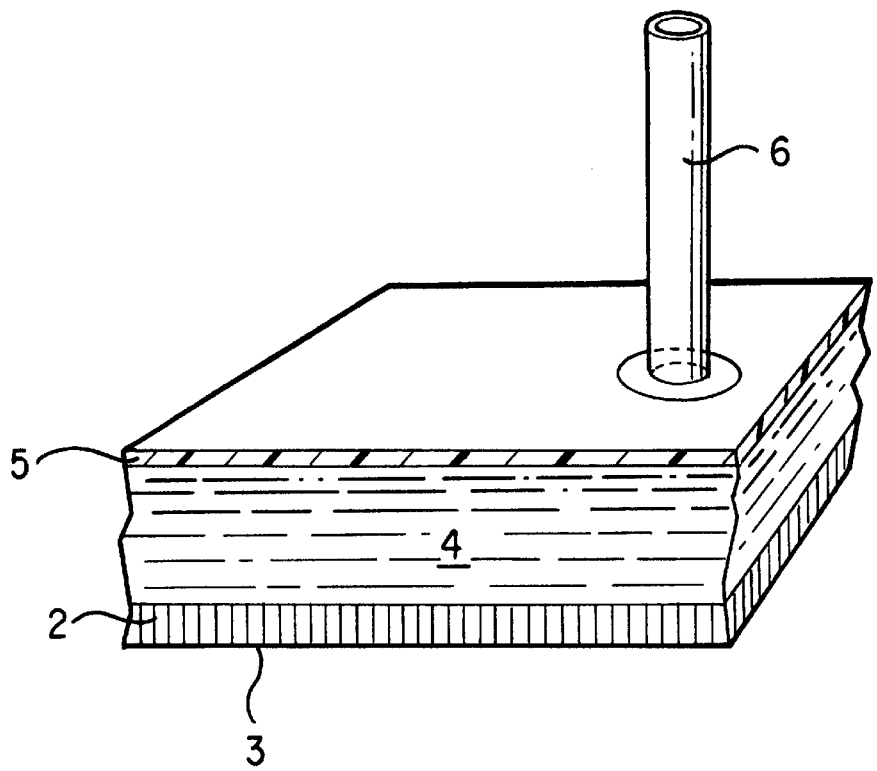
Figure 2:
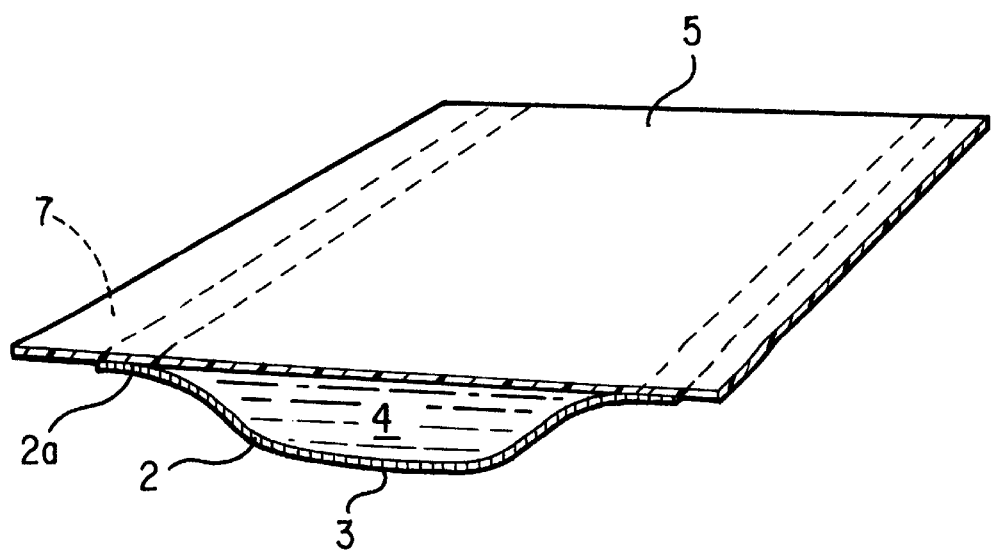
Figure 3:
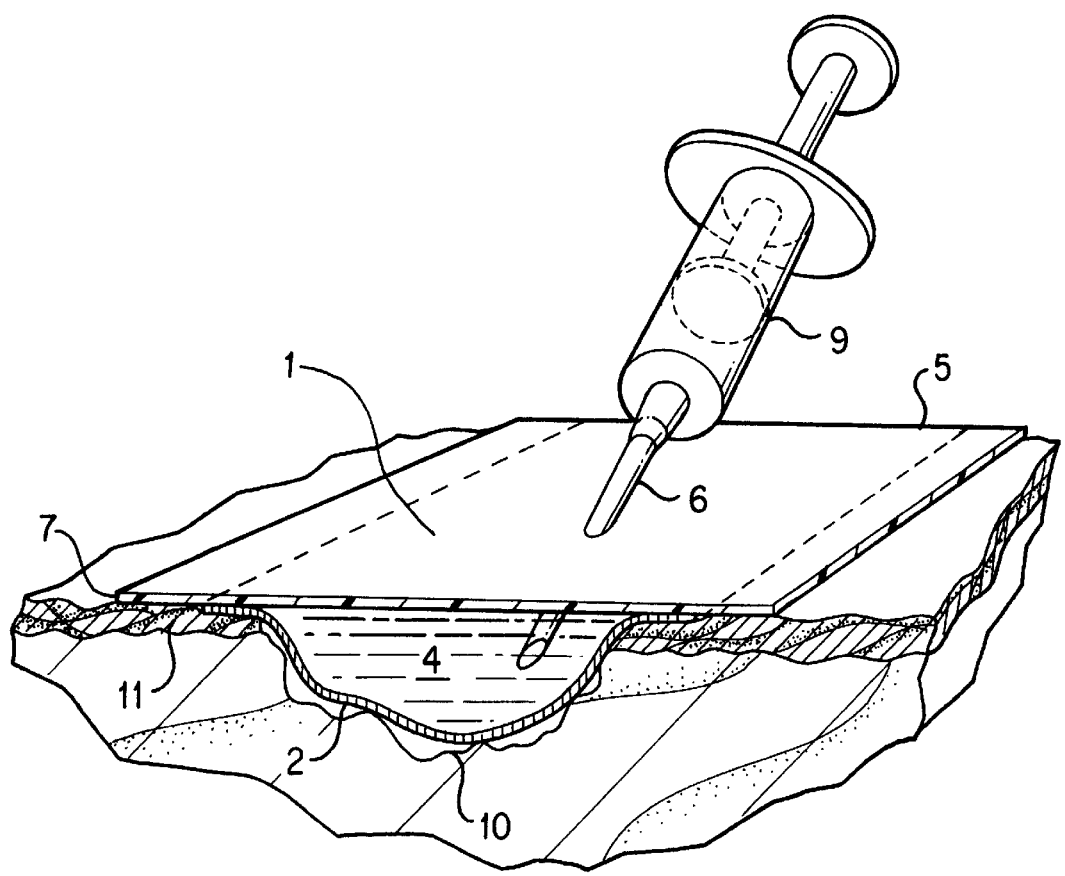
Figure 4:
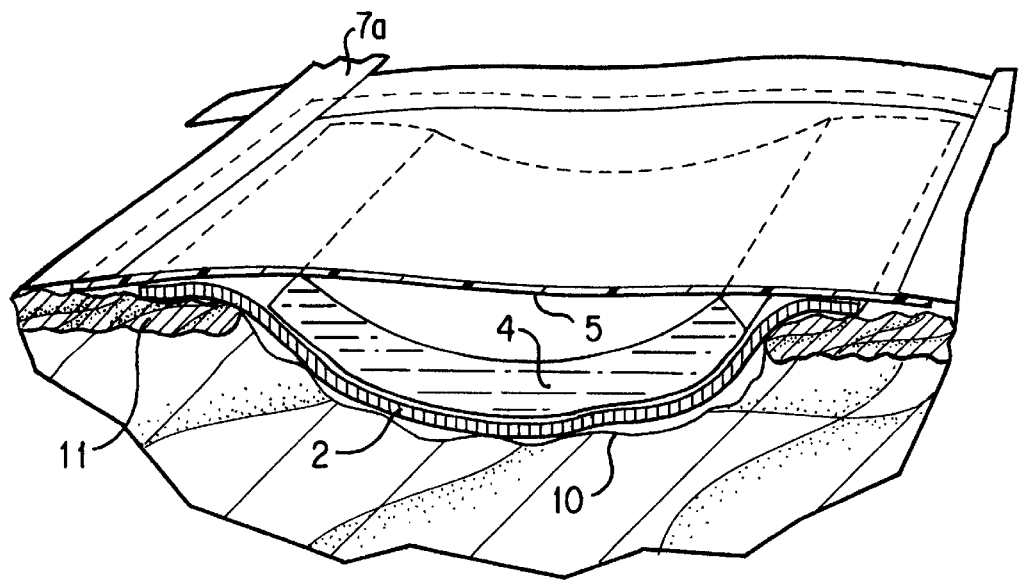

The present invention should be more fully understood when the specification herein is taken in conjunction with the drawings appended hereto wherein:

FIG. 1 schematically depicts the cross-section of the bioreactor dressing and its main components;

FIG. 2 shows a partial cross-section of the flat poach design of bioreactor dressing from Example 1;

FIG. 3 shows application of the flat poach bioreactor dressing to a wound;

FIG. 4 shows an assembly of membrane design bioreactor dressing from its components on the wound;

FIG. 5 schematically shows construction of the membrane bioreactor dressing with enclosed protective layer and an exchangeable hydrogel reservoir layer; and, FIG. 6 schematically shows a tubular design of the bioreactor dressing and its basic components.

DETAILED DESCRIPTION OF THE PRESENT INVENTION

This invention is based on our recognition that a dressing's function resembles the function of a membrane bioreactor in many ways. A healing process involves growth of tissue and migration, proliferation and differentiation of cells that have to be protected, supported and nutrified regardless of growing in vitro or in vivo.

The dressing according to our invention is constructed to form a bioreactor optimized to support proliferation of keratinocytes and other cells in the epidermis, as well as performing other desirable functions:

protection from an external trauma moisture control in the wound bed control of pH control of salt concentration control of oxygen concentration thermal regulation infection control supply of nutrients supply of antibiotics, vasodilatants, vasoconstrictors, steroids and other bioactive substances supply of growth factors, hormones, enzymes, stimulants and other biomolecules This dressing's primary function is to occlude the wound, to control its environment and to promote healing by supporting the growth of keratinocytes, fibroblasts and other cells within the wound. Its secondary but important function is to support growth of keratinocytes in vitro so that they can be applied to the wound as a part of the dressing.

The dressing is schematically depicted in FIG. 1. It consists of the following components:

Transport layer 2 designed for delivery of substances to and from the wound.

The transport layer contains the cultivation surface 3 that is in the direct contact with the wound. Optionally, the cultivation surface has variable adhesion for cells, being adhesive under in vitro cultivation conditions and capable of releasing the cells after its application to a wound.

Reservoir layer 4 adjacent to the transport layer 2. The liquid in the reservoir layer is optionally exchangeable or replaceable by another liquid, as required for the optimum wound healing. Optionally, the dressing contains means 6 for exchange of fluids in the reservoir layer.

Optionally, the dressing contains an outside polymeric protective layer 5 adjacent to the fluid reservoir zone 4.

The dressing design and function is further illustrated by the following description of its essential components.

1. TRANSPORT LAYER.

This layer is used for transport of water, nutrients and biomolecules to and/or from the wound as well as a support for the cell growth and proliferation.

The transport layer comprises at least one layer of a permeable polymeric medium that has average water content at least 40% by weight and that is permeable for water soluble compounds with molecular weight up to at least 1000 Daltons. Polymeric media meeting these characteristics are permeable enough to pass the basic nutrients, metabolites, water, salts and oxygen. This allows the control of the wound bed conditions. At the same time, this polymeric medium is a barrier for compounds for cells and all infectious agents, such as spores or viruses.

More preferably, this layer has average water content higher than 60% by weight and is permeable for water-soluble compounds with molecular weight up to at least 5000 Daltons. Permeable polymeric medium with these characteristics allows very good control of the wound bed conditions as well as flow of nutrients and metabolites, including some of the biomolecules important for cell growth and proliferation.

The permeable polymeric medium is preferably soft and elastomeric as to comply readily with the wound bed surface. Preferred materials have elongation at break higher than 100% and preferably over 250%.

According to another preferred embodiment, the transport layer is capable of hydraulic permeability. In this case, aqueous liquids can be transported through the layer by action of a pressure gradient. The hydraulic mass transport is often more effective than the diffusive mass transport and less dependent on molecular weight of the permeant.

The permeable polymeric medium can be made of a microporous polymer, such as ultrafiltration or microfiltration membranes well known to those skilled in the art. The open pores filled with water create the pathway for transport of nutrients and biomolecules but they are too small to pass cells, spores or viruses. Preferably, the polymer component is at least partially wettable with water and resistant to an irreversible protein adsorption.

The polymeric component can be of a natural or synthetic origin. Particularly preferred permeable polymeric media are hydrogels with a water content over 40% by weight and preferably over 60% by weight. Hydrogels allow transport of water-soluble substances through free water in their structure, without relying on physical pores that can be clogged by cells, denatured proteins or particles. In addition, hydrated hydrogels are generally soft and can well comply with the wound surface. Homogenous hydrogels are also transparent as to allow the visual inspection of the wound without removing the dressing. Examples of suitable hydrogels are polyvinylalcohol-based hydrogels, such as those described in the U.S. Pat. No. 4,663, 358, hydrogels based on partially hydrolyzed polyacrylonitrile or partially aminolyzed polyacrylonitrile, such as described in the U.S. Pat. No. 4,331,783; 4,337,327; 4,370,451; 4,379,874; 4,420,589; 4,943,618, and 5,252,692 polyvinylpyrrolidone; polyethylene oxide; hydrophilic polyurethane segmented copolymer, such as those described in the U.S. Pat. Nos. 5,120,816, or 5,688,855. Preferred are hydrogels in which the water content is primarily controlled by physical crosslinking rather than covalent network, as can be readily established from swelling data (For instance, swelling in organic solvents can be used to establish the extent of the physical crosslinking. Those hydrogels that rely only on their covalent network do not increase their swelling substantially if the water is partly or fully exchanged for a good solvent of the polymeric component).

Suitable permeable polymeric media are also composites containing hydrogels as one of the component, such as those described and referenced in P. Hron et al, Biomaterials 18, pp. 1069–1073 (1997).

The upper limit on the water content is limited only by its mechanical properties. Since the main function of the layer is the diffusive transport, and since permeability for aqueous solutes increases with water content, it is advantageous to use a hydrogel with a high water content. At the same time, this polymeric medium is advantageously a barrier for compounds with molecular weight higher than about 250,000 Daltons.

Many hydrogels, such as hydrophilic polyurethane's can be used with water content between 70 and 80% of water. Such hydrogels are permeable for water-soluble compounds of molecular weight as high as 60,000 Daltons. Certain polyvinylalcohol-based hydrogels can be used at water content as high as 80 to 90% by weight of water. Hydrogels based on partially hydrolyzed polyacrylonitrile have sufficient strength for this purpose at water content as high as 95% by weight. Such hydrogels are permeable for water-soluble compounds of a molecular weight as high as 100,000 Daltons or even more. This permeability is highly desirable because it allows controlled delivery of nutrients and biologically active compounds to the wound.

The cultivation layer has its outer surface that is called hereinafter "the cultivation surface". This surface has at least two functions: it is used as the release and seeding surface, and as a cultivation surface. For the first function, it is an advantage if this surface is highly hydrophilic and well wettable with water so that if fully hydrated, it does not adhere to the wound bed and can be removed readily when needed. On the other hand, in its cultivation function the surface has to provide a support for attachment of keratinocytes. Keratinocytes cannot attach well to a highly hydrated surface but they can grow well on substantially hydrophobic or partly hydrophobic surfaces. From this viewpoint, the cultivation surface should be substantially hydrophobic with a limited wettability with water. Once the keratinocytes are grown, it is an advantage to release them from the surface and seed them to the wound. In this case, it is again an advantage if the surface is highly hydrated and completely wettable with water. The surface has to be carefully selected to have the right wettability to be able to perform both the cultivation function and release function. Cultivation surfaces that can satisfactorily perform the cultivation function have typically wetting angle with water higher than 20 degrees and advantageously higher than 35 degrees. To be able to release the cells, the surface should have a wetting angle lower than 90 degrees and advantageously lower than 60 degrees. Even in this range, the final performance will be compromised because the release works best at wetting angles with water close to zero (less than 10 degrees) in which case keratinocytes cannot attach to the surface well enough. To reconcile the opposite requirements of the two functions, the preferred hydrogels are those with so called "wetting angle hysteresis", i.e. those with higher wetting angle for advancing than receding liquid. If the difference between advancing and receding angle is larger than about 10 degrees, the hydrogel can usually accommodate the contradicting requirements for the cell cultivation and cell seeding.

Both wetting properties and permeability depend on hydration so that usually highly wettable materials are highly permeable for aqueous solutes, and vice versa. Therefore, selection of a highly permeable material with a relatively hydrophobic surface is not a trivial matter.

From the viewpoint of the present invention, one group of preferred materials are hydrogels with equilibrium water content higher than 75% and preferably higher than 85% with surface modified to be relatively hydrophobic. Such surfaces have a wetting angle with water higher than 20 degrees and preferably higher than 30 degrees. The surface modification can be performed by numerous methods well known to those skilled in the art, such as the surface sililation or acetylation of a suitable hydrogel.

Particularly effective methods for surface hydrophobization are those based on surface phase separation in hydrogels that contain both polar and non-polar groups or domains. Such a separation can be achieved by solidification of hydrogel-forming solutions on a hydrophobic substrate, such as polyethylene or polypropylene. Hydrogels capable of such a phase separation are based on copolymers containing both hydrophilic and hydrophobic units, particularly block copolymers. This class includes several types of polymers. One type are multiblock copolymers based on partial hydrolysis or aminolysis of polyacrylonitrile. Another is based on hydrolysis of polyvinylalcohol esters or acetals. Still another type is based on segmented polyurethane's, polyureas, polyesters or polyamides, particularly those containing polyethylenoxide hydrophilic segments.

The preferred hydrogel is one that is able to change its surface properties (represented by surface free energy and measured, for instance, by the wetting angle with water) in response to external conditions (such as temperature, pH, osmolarity, electric potential, presence of liquid water, etc.). The hydrogel surface can be thus converted from partly hydrophobic (as suited for keratinocyte cultivation) to highly hydrophilic (as suited for keratinocyte release, seeding and its support by diffusion of nutrients), and vice versa. Polymers capable of changing their hydrophilicity in response to a change in external conditions are well known to those skilled in the art. Preferred are polymers that can change from hydrophilic to hydrophobic form by increasing temperature over certain inversion temperature $T_i$ that is lower than 40° C. Preferably, the inversion temperature is between 20° C. and 35° C. Examples of polymers having this property are copolymers of ethyleneoxide and propyleneoxide; copolymers of vinylalcohol with vinylacetate; polymers and copolymer of N-substituted acrylamide and methacrylamide, particularly N-isopropylacrylamide; polymers and copolymers of vinylmethyloxazolidone, and polymers and copolymers of methylvinylether.

Another preferred group are polymers capable of changing from hydrophobic to hydrophilic form in response to a change of pH. Particularly preferred are polymers carrying both anionic and cationic groups and capable of forming internal salts in the pH range between about 3 and 8. Examples of such polymers are aminolyzates of polyacrylonitrile described in the U.S. Pat. No. 5,252,692.

The above mentioned polymers can be employed as blends with other hydrophilic and hydrogel-forming polymers or hydrogels if crosslinked by covalent bonds or strong physical interactions. Such hydrogels can be barriers for certain types of substances at one set of conditions while becoming highly permeable to medium at another set of conditions.

More preferably, these polymers are employed as grafts on surface of the permeable polymer media, particularly on its cultivation surface. Grafting can be achieved by many methods known to those skilled in the art, and it is not the object of this invention to teach new grafting techniques.

Adhesivity for keratinocytes can be improved by pre-adsorption of proteins, lipoproteins or glycoproteins such as albumin, fibrinogen, fibronectin, laminin or collagen, on the cultivation surface. The adsorbed protein conditions the surface for adhesion of cells. Advantageously, the deposited protein is rendered insoluble in water by its denaturing or a slight crosslinking. The denaturing can happen spontaneously during adsorption of proteins on surfaces with hydrophobic domains or groups. The denaturing can be also facilitated by exposure of deposited protein to heat, organic solvents, etc. The protein deposition can be achieved by various techniques, such as incubation of the transport layer in a solution containing proteins, lipoproteins or glycoproteins, preferably at an elevated temperature or while cycling between low and high temperatures. The protein layer can be deposited on the cultivation surface by ultrafiltering a protein solution through the transport layer. In addition or instead of glycoproteins, suitable carbohydrates or glycolipids can be attached to or deposited onto the cultivation surface to support and to facilitate the cell attachment and proliferation. It is well known to those skilled in the art that specific carbohydrates can mediate adhesion of specific cells. Such carbohydrates can be employed as part of the cultivation surface.

The transport layer can be used in various shapes and geometry. Their footprint can be circular or rectangular, and they can be shaped as a flat sheet, as a poach, as a tubing, e.t.c. The poach or tube shape is used mostly for dressings designed to fill deep, irregular chronic wounds.

2. RESERVOIR LAYER

This zone contains an aqueous liquid which is in a permeable contact and osmotic equilibrium with the transport layer. The main role of this layer is to be a source of water, nutrients, oxygen, salts, biomolecules and other substances required for cell growth and wound healing. Another role is to be a container for excess of the liquids (e.g., exudate) transported from the wound. Still another role is a thermal regulation and cooling to the wound. And finally, the liquid provides a cushion protecting the wound from a mechanical trauma. The liquid can be immobilized in a soft sponge or in the form of a soft gel or a gel slurry.

This layer can be equipped by optional means for exchange of the liquid within and to adjust its composition to the changing healing requirements. The liquid exchange can be done in various ways. For instance, the liquid can be withdrawn, added or replaced through a valve or through a septum by a syringe. The liquid reservoir layer can be also connected to an external liquid container, pump, etc. and the liquid can be exchanged or circulated continuously. The liquid can also be immobilized in the form of a replaceable insert formed by a sponge or a gel. The liquid-containing insert can be replaced as needed. The reservoir layer can also contain gases in addition to liquids. For instance, oxygen can be used to support healing, carbon dioxide can be used to support cell cultivation, etc.

The properties of the fluid inside the reservoir layer are affecting the condition in the wound. For instance, if the liquid is hypertonic due to a high concentration of dissolved polymers larger than permeation limit of the cultivation zone, it will draw liquid from the wound bed and act as an absorbent dressing. If the liquid will be hypotonic, it will moisturize the wound bed and facilitate the release of the dressing from the newly formed tissue. Likewise, the liquid can contain increased concentration of oxygen, salts, antibiotics, tissue growth stimulators or other substances that are necessary in the given moment to support healing. What is important is the possibility to change the wound conditions without removing the dressing and exposing thus the wound to an infection or injury. Volume and pressure of the liquid can be used to achieve the contact with the wound bed even in deep, irregular wounds. The volume of the dressing can be changed over time to comply with the healing of the wound.

The liquid can be also a source of stimulants and other biomolecules promoting growth of keratinocytes and other tissue cells. Many of these factors are unstable or not available in the pure form. In that case, the bioreactor dressing can be used to generate such biomolecules in situ by incorporating appropriate source cells into the liquid. For instance, it is possible to cultivate 3T3 fibroblasts in the liquid reservoir layer. Their metabolic products can then permeate through the transport layer to the cultivation surface to be available for support keratinocyte growth. Another possible sources of biomolecules can be plasma, green microalgae etc.

3. OPTIONAL PROTECTIVE LAYER

The outermost layer (adjacent to the Reservoir Layer) can be made from a substantially impermeable plastic foil. Its role is to protect the underlying structures from a mechanical damage, from contamination and from a gross loss of liquids. A moderate water loss due to evaporation of water through the foil is usually inconsequential. It is sufficient if the protective layer is a reliable barrier for compounds larger than about 50 Daltons.

It is desirable that the zone is transparent and not obstructing view of the wound. Examples of suitable materials are polyolefines; soft acrylic resins; polyurethane's; plasticized PVC; silicone and other synthetic elastomers.

This layer can have a larger footprint area than the other two zones. The extra area can be covered with a suitable skin adhesive for fixing the dressing and sealing the wound.

This layer can be also equipped with means for the liquid exchange in the reservoir layer: a valve, a septum, a watertight linear zipper, etc.

The invention is illustrated by the following Examples. The Examples are not intended to describe all possible implementation of the invention nor limit its scope.

EXAMPLE 1

The dressing 1 is described in the FIG. 2 where 2 is the transport layer from the permeable material described below; 5 is the protective layer that is connected to the periphery zone 2a of the transport layer 2, forming a space wherein an aqueous liquid comprising a hydrogel dispersion is confined. That space is filled with the liquid forms the Reservoir Layer 4.

The protective layer 5 is made of a commercial foil of clear polyurethane polymer covered by a thin layer of acrylic pressure-sensitive adhesive.

The transport layer 2 is made from a highly permeable acrylic hydrogel based on a partially hydrolyzed polyacrylonitrile. The partial hydrolysis of polyacrylonitrile is carried out by a basic catalyst and yields a multiblock copolymer containing residual nitrile groups, sodium carboxylate groups, amidine groups and amide groups in such a proportion that the liquid content in the hydrogel is more than 90% by weight in the equilibrium with 0.9% by weight of NaCl aqueous solution. The polymer can be dissolved in an aqueous solution containing 55% by weight of NaSCN.

10% by weight of the polymer solution in NaSCN is cast on a pre-cooled polypropylene plate to form a thin layer. After 30 minutes, the solution is coagulated by immersion into isotonic saline at ambient temperature. The hydrogel foil thus formed is carefully stripped from the support and washed in fresh saline. The resulting foil has the liquid content 92% by weight and two distinctly different surfaces: the surface that is formed against the polypropylene plate and the surface that is formed in a direct contact with the coagulating liquid. The former surface is distinctly less hydrophilic than the later. The more hydrophobic surface is designated as the "cultivation surface" 3.

A square 2"×2" of the hydrogel foil is dye-cut and its edge 2a about 0.2" wide is glued to the pressure-adhesive layer of the protective layer 3 using a cyanoacrylate adhesive. The hydrogel foil now forms the transport layer 2 and its cultivation surface 3 faces away from the protective layer 5. A sealed space 4 is formed between the transport layer 2 and the protective layer 5. The protective layer is cut to a square 4"*4" so that 1" wide adhesive zone 7 is created for fixation of the dressing to the patient's skin.

A solution A of the following composition is created:

Eagle's MEM solution in Hank's buffered saline is modified by addition of 0.12 grams of sodium pyruvate per 1 liter and by adjustment of $NaHCO_3$ concentration to 1 gram per 1 liter of the solution. Moreover, the following components are added per 1 liter of the solution: 100 ml of bovine serum, 0.5 mg of insulin, 50 mg/l of cholera toxin $10^{-10}$M solution, 5000 nanograms per liter of epidermal growth factor (EGF), 200,000 units of penicillin and 100,000 units of streptomycin.

The solution A is thickened by addition of 5 grams of a superabsorbent hydrogel (a crosslinked potassium polyacrylate) per 1000 grams of the solution. The dispersion is mixed in a high-shear blender to form a highly viscous cultivation medium. The cultivation medium is injected into the space 4 through a gauge 18 hypodermic needle 6 to form the Reservoir Layer. The puncture is then sealed by an adhesive tape.

The dressing is packaged by sealing into a water-impermeable plastic poach and sterilized by gamma irradiation. The dressing can be applied directly to the wound to protect it and to promote tissue regeneration and wound healing. The dressing can be applied with the empty space 4, i.e. prior the injection of the solution A. The application is schematically depicted in FIG. 3 where 1 is the dressing, 10 is the wound bed and 11 is the intact skin around the wound. Once the dressing is in place, the cultivation medium is injected by the syringe 9 through the needle 6 into the space 4 to form the reservoir layer. The volume of the solution A is selected so that the transport layer 2 essentially complies with the wound surface, as schematically depicted in FIG. 3. After the cultivation medium is injected, the wound is sealed by pressing the adhesive 7 to the skin 11. In the case that the wound is producing an exudate, the isotonic fluid can be exchanged for a hypertonic solution B containing a high-molecular water-soluble polymer. The exchange can be performed at any point during the healing process.

In this example, the hypertonic solution B is formed by a 5.5% by weight aqueous solution of dextrane polymer with molecular weight 260,000. In addition to the dextrane, it contains all the components of the solution A. The exchange of the cultivation medium for the hypertonic solution B can be achieved using a hypertonic needle and a syringe. The exchange is performed in situ, without removing the dressing from the wound and exposing it to an infection. once the exudation ceases, the solution B can be replaced by the solution A or by another liquid of an appropriate composition.

EXAMPLE 2

The dressing from the Example 1 can be used for keratinocyte cultivation for wound healing. The transport layer is modified by exposure to bovine serum for 48 hours from the cultivation surface side. The dressing is then surface dried, packaged into a semipermeable poach and autoclaved for 30 minutes at 123° C. The deposited layer of denatured proteins on the cultivation surface improves adhesion of cells in the subsequent steps. The procedure is carried out in the following steps:

1) A biopsy sample is taken from the skin of a patient suffering by a chronic or acute wound. The skin sample is treated with trypsin to release keratinocytes.

2) The dressing's 1 cavity 4 is filled with the solution A and placed into a Petri dish filled with the solution A. The dressing is turned so that the cultivation surface faces upwards. 3T3 mouse fibroblasts are irradiated by a lethal dose of Gamma radiation and seeded onto the cultivation surface.

3) After 24 hours in an incubator at 37° C., keratinocytes obtained from the biopsy are seeded onto the fibroblast layer and cultivated for another five days.

4) After 5 days, the cultivation surface is covered by colonies of keratinocytes. The dressing is removed from the Petri dish, placed against the wound and secured by an adhesive tape. The adhesive rims 6 are pressed against the skin to seal the wound.

5) Progress of the healing is observed through the transparent dressing 1. The cultivation medium in the reservoir layer 4 is replaced from time to time for a fresh one or for a different solution as needed to remove excess of exudate, to control an infection etc. The changes in the liquid in the reservoir layer 4 are carried out without removing the dressing from the wound.

6) Once the wound is closed by the newly formed epidermis, an extra isotonic saline is injected into the reservoir layer to facilitate the release, and the dressing is removed from the patient's skin.

EXAMPLE 3

The transport layer is made from a hydrogel prepared by the following method:

100 weight parts (w.p.) of 2-hydroxyethylmethacrylate monomer (HEMA), 450 weight parts of water, 450 weight parts of ethyl alcohol and 3 w. p. of hydrogen peroxide was stirred for 8 hours at 65° C. under reflux condenser and nitrogen protective atmosphere. The resulting viscous solution is cooled and poured into an excess of water. The white precipitate is formed and washed in deionized water for several days. The purified uncrosslinked HEMA polymer (PHEMA-S) is cut to small pieces and dried at 60° C. to constant weight. The resulting glassy polymer is ground to a crude powder and stored in closed containers.

10 w.p. of the PHEMA-S powder is dissolved in 80 w.p. of ethyl alcohol, 5 parts of water, 5 parts of 1,2 propylene glycol and 0.1 part of phosphoric acid. This solution is spread into a thin layer over a polyester mesh, let dry at 60° C. for 3 hours and then heated to 120° C. for another 2 hours. The resulting reinforced hydrogel layer is washed thoroughly in distilled water. The water content in equilibrium is 41% by weight.

The membrane bioreactor dressing is assembled from components as depicted in FIG. 4 and used as described below:

The hydrogel transport layer 2 is soaked in the solution A from Example 1 for 3 days and then used for cultivation of keratinocytes in vitro as described in Example 2.

The reservoir layer 4 is formed by a polyurethane sponge with open pores soaked in the cultivation medium from Example 1. The protective layer 5 is created from a polyethylene foil. After the keratinocyte cultivation is finished, the hydrogel layer 2 is cut to the size and shape of the wound and applied against the wound bed 10. Secondly, the reservoir layer 4 is cut to a similar shape and size and applied over the transport layer 2. Thirdly, the protective polyethylene foil 5 of a larger size than the reservoir layer is applied over it and secured in place by an adhesive tape 7a.

The wound can be inspected by removing the foil and the sponge without removing the transport layer. If needed, a sponge with a different composition can be applied over the transport layer (e.g., a sponge soaked with a hypertonic solution B from Example 1 to remove excess of exudate, or an antibiotic solution to control an infection in the wound).

The transport layer is kept on the wound until its closure by a new epidermal layer is formed. After that, the hydrogel layer is stripped and disposed. The stripping can be facilitated by irrigation with an isotonic saline.

EXAMPLE 4

25 w.p. of dry PHEMA-S from EXAMPLE 3 is dissolved in a mixture of 120 w.p. of ethyl alcohol and 60 w.p. of glycerol. After the polymer dissolution, 25 w.p. of HEMA monomer, 0.15 w.p. of ethyleneglycoldimethacrylate (EGDMA) and 0.25 w.p. of dibenzoylperoxide is added to the solution and mixed thoroughly. The mixture is then stored in freezer in a dark bottle.

The mixture is spread over a cellulosic microporous membrane with nominal pore size 10 microns and heated to 70° C. in oven under nitrogen for eight hours. After that, the membrane is washed in distilled water. The cellulosic membrane is impregnated with a microporous crosslinked PHEMA.

In the next step, the membrane is grafted by IsoPropyl-N-AcrylAmide (IPNAA) using activation of OH groups by trivalent cerium ions. The membrane is immersed into a 0.1% by weight solution of cerium nitrate and 10% by weight of IPNAA under nitrogen for 60 minutes at ambient temperature. After that, grafted membrane is thoroughly washed in a cold distilled water. The grafts are causing that the surface is more hydrophobic and cell-adhesive at a temperature over 33° C. and more hydrophilic and non-adhesive at lower temperatures.

The space 4 is formed by attaching the transport layer 2 to a poach 5 with a cut-out window 5a one face and closed on its side by a linear zipper 5b, as shown in FIG. 4. The reservoir layer is formed by a slab 4a of an agar gel soaked in the solution A that is inserted into the space 4.

The keratinocytes are grown on the cultivation surface 3 at 37° C. as described in Example 2.

The dressing with cultured keratinocytes is applied against a chronic or acute wound. The keratinocytes are released into the wound bed by replacing the agar gel for a cold insert, such as a cold pack or a poach filled with crushed ice and water.

In the case that there is an exudate, a partially dehydrated hydrogel can be inserted into the space 4.

EXAMPLE 5

This Example describes a bioreactor dressing designed to fill deep, irregular wounds, such as deep diabetic ulcers. It is schematically depicted in the FIG. 6 where 2 is the transport layer in the form of a hydrogel tubing that passes through the protective layer 5. There is the cultivation surface 3 on the outer surface of the tubing 2. The tubing cavity 4 is filled with a liquid and plays the role of the reservoir layer. The filled volume in the wound can be changed as required (e.g., by changing pressure inside the flexible tubing 2, or by pulling a part of the tubing 2 out of the wound bed through the orifice in the protective layer 5. The tubing 2 is equipped by connectors 6a, 6b to facilitate exchange of the liquid inside the reservoir layer 4. The tubing 2 can be partially pulled out of the wound through the protective layer 5, the protective sleeve 5c and the sealing cuff 5d. The thin-walled tubing 2 is made by extrusion of a hydrophiic polyurethane hydrogel of the composition describe in the U.S. Pat. No. 5,120,816, Example E1, Table 3. The tubing containing 85% by weght of water in equilibrium is thoroughly washed in distilled water, then coated with a layer of poly(methylvinylether) (PVME) by dipping the tubing into 50% by weight PMVE Solution in water. The coated tubing is then dried and irradiated by the dose of 2.5 MRad of gamma radiation. This crosslinks the PMVE coating and achieves its adhesion to the surface of the tubing. The PMVE layer form the cultivation surface. It is cell-adhesive at the cultivation temperature of 37° C. but cells can be released by running a cold solution through the tubing. The decreased temperature also helps to decrease the pain.

EXAMPLE 6

The tubing of the dressing from Example 5 is filled with 3T3 mouse fibroblasts dispersed in a cultivation medium. The tubing is then immersed into a dispersion of human keratinocytes in the solution A at 35° C. The dispersion is gently stirred to prevent cell sedimentation for 5 days. Then the dressing is applied to a deep ulcer so that the hydrogel tubing 2 substantially fills the wound. The ends of the tubing are attached to an infusion set for changing the solution in the tubing as required by the wound healing. As the healing progresses and the wound cavity diminishes, the tubing is gradually pulled out of the wound bed. The tubing removal is facilitated by feeding a cold solution into the tubing at an increased pressure. The solution penetrates through the hydrogel wall due to its hydraulic permeability while decreased temperature renders the cultivation surface non-adhesive to the cells and tissue.

What is claimed is:

1. A method of wound treatment comprising the following steps:

a) placing a wound dressing comprising a first layer being a transport layer in the direct contact with a wound and including at least one layer of a permeable polymeric media containing, in equilibrium with body fluids, at least 40% by weight of liquid, being impermeable for infectous agents of any kind and being permeable to water soluble substances having molecular weight up to at least 1000 Daltons; and, a second layer being a fluid reservoir layer that is adjacent to the transport layer and is capable of containing between 40% and 100% of its volume of an aqueous liquid, wherein the transport layer and reservoir layer are permeably interconnected for aqueous solutions and are in a substantial osmotic equilibrium and, wherein said transport layer has at least one cultivation surface that is adhesive.

2. A bioreactor wound dressing, which comprises:

a.) a first layer being a transport layer in the direct contact with a wound and including at least one layer of a permeable polymeric media containing, in equilibrium with body fluids, at least 40% by weight of liquid, being impermeable for infectious agents of any kind and being permeable to water soluble substances having molecular weight up to at least 1,000 Daltons, wherein said transport layer has at least one cultivation surface that is adhesive to cultured tissue cells under conditions suitable for cell cultivation; and, b.) a second layer being a fluid reservoir layer that is adjacent to the transport layer and is capable of containing between 40% and 100% of its volume of an aqueous liquid, wherein the transport layer and reservoir layer are permeably interconnected for aqueous solutions and are in a substantial osmotic equilibrium.

3. The wound dressing according to claim 2 wherein said permeable polymeric medium contains, in equilibrium with body fluids, at least 60% by weight of liquid and is permeable for water soluble substances having molecular weight up to at least 5,000 Daltons.

4. The wound dressing according to claim 2 wherein said permeable polymeric medium is a hydrogel.

5. The wound dressing according to claim 4 wherein said hydrogel is a physically crosslinked hydrogel.

6. The wound dressing according to claim 2 wherein said cultivation surface has a wetting angle with water higher than 20 degrees.

7. The wound dressing according to claim 2 wherein said cultivation surface is cell adhesive at a temperature higher than its inversion temperature and non-adhesive to cells at a temperature lower than its inversion temperature, wherein said inversion temperature is lower than 40° C.

8. The wound dressing according to claim 2 wherein said cultivation surface contains at least one organic compound selected from group consisting of proteins, lipoproteins, glycoproteins, glycolipids and carbohydrates.

9. The wound dressing according to claim 2 wherein said dressing includes an additional protective layer of polymeric material that is substantially impermeable to substances with a molecular weight higher than 50 Daltons, said protective layer being the outermost layer of the dressing, and wherein the said fluid reservoir layer is a space between said protective layer and said transport layer and contains an aqueous liquid.

10. The wound dressing according to claim 2 wherein said reservoir layer is a hydrogel swelled with an aqueous liquid.

11. The wound dressing according to claim 2 wherein said transport layer is a hydrogel that is capable of changing its surface properties in response to a change of external conditions, selected from the group consisting of a change of temperature; a change of pH; and a change of osmolarity.

12. The wound dressing according to claim 2 wherein said fluid reservoir layer contains at least one type of biologically active compound.

13. The wound dressing according to claim 2 wherein said transport layer and said fluid reservoir layer are optically transparent.

* * * * *